United States Patent
Gisiger (10) Patent No.: US 10,835,160 B2
(45) Date of Patent: Nov. 17, 2020

(54) APPARATUS AND METHOD FOR NON-INVASIVELY DETERMINING THE CONCENTRATION OF AN ANALYTE

(71) Applicant: Radiometer Basel AG, Basel (CH)

(72) Inventor: Pierre-Alain Gisiger, Courroux (CH)

(73) Assignee: RADIOMETER BASEL AG, Basel (CH)

( * ) Notice: Subject to any disclaimer, the term of this patent is extended or adjusted under 35 U.S.C. 154(b) by 675 days.

(21) Appl. No.: 15/535,545

(22) PCT Filed: Dec. 14, 2015

(86) PCT No.: PCT/EP2015/079523
§ 371 (c)(1),
(2) Date: Jun. 13, 2017

(87) PCT Pub. No.: WO2016/096682
PCT Pub. Date: Jun. 23, 2016

(65) Prior Publication Data
US 2017/0360339 A1 Dec. 21, 2017

(30) Foreign Application Priority Data

Dec. 15, 2014 (DK) .................................. 2014 00725

(51) Int. Cl.
*A61B 5/1477* (2006.01)
*A61B 5/1491* (2006.01)
*A61B 5/145* (2006.01)

(52) U.S. Cl.
CPC ........ *A61B 5/14542* (2013.01); *A61B 5/1477* (2013.01); *A61B 5/1491* (2013.01); *A61B 2562/0271* (2013.01); *A61B 2562/04* (2013.01)

(58) Field of Classification Search
CPC . A61B 5/14542; A61B 5/1477; A61B 5/1491; A61B 2562/0271; A61B 2562/04
(Continued)

(56) References Cited

U.S. PATENT DOCUMENTS 4,183,248 A * 1/1980 West .................. G01K 1/18
   338/23
6,773,405 B2 * 8/2004 Fraden .................. A61B 5/01
   600/549
(Continued)

FOREIGN PATENT DOCUMENTS

CN      102472719 A    5/2012
EP      0 039 243 A2   11/1981
(Continued)

OTHER PUBLICATIONS

Parker, D. et al., "A Transcutaneous $P_{O2}$ Electrode Incorporating a Thermal Clearance Local Blood Flow Sensor," Acta anaesth. scand., Suppl., pp. 33-39 (1978).
(Continued)

*Primary Examiner* — Navin Natnithithadha
(74) *Attorney, Agent, or Firm* — Finnegan, Henderson, Farabow, Garrett & Dunner, LLP (57) ABSTRACT

A sensor and an apparatus for non-invasive measurement of an analyte concentration, the apparatus comprising: a first thermal sensor operable to determine a temperature indicative of a temperature at a location on a skin of a subject, an analyte sensor operable to generate a measurement indicative of a concentration of the analyte, a heater; a controller operable to receive a temperature signal from at least the first thermal sensor and to adjust the heater to maintain a thermal equilibrium at said location on the skin; and a processor configured to convert the measurement to a calculated analyte concentration value at a predetermined temperature.

18 Claims, 4 Drawing Sheets

(58) Field of Classification Search
USPC .......................................... 600/309, 345–366
See application file for complete search history.

(56) References Cited

U.S. PATENT DOCUMENTS

| | | | | |
|---|---|---|---|---|
| 8,172,459 | B2* | 5/2012 | Abreu | ................... A61B 5/6814 374/208 |
| 8,328,420 | B2* | 12/2012 | Abreu | ...................... A61B 5/01 374/208 |
| 8,834,020 | B2* | 9/2014 | Abreu | ................... A61B 5/6814 374/121 |
| 9,119,530 | B2* | 9/2015 | Abreu | ................... G01K 13/002 |
| 9,316,594 | B2* | 4/2016 | Kane | ....................... G01N 21/80 |
| 2002/0062070 | A1 | 5/2002 | Tschupp et al. | |
| 2005/0209516 | A1 | 9/2005 | Fraden | |
| 2007/0106172 | A1* | 5/2007 | Abreu | ................... A61B 5/0002 600/549 |
| 2009/0105605 | A1* | 4/2009 | Abreu | ................... A61B 5/0046 600/549 |
| 2012/0316459 | A1* | 12/2012 | Abreu | ................... A61B 5/6814 600/549 |
| 2013/0317368 | A1 | 11/2013 | Warren et al. | |

FOREIGN PATENT DOCUMENTS

| | | |
|---|---|---|
| EP | 0 077 073 A2 | 4/1983 |
| GB | 2 100 864 A | 1/1983 |
| JP | 55-88749 | 7/1980 |
| JP | 58-501659 | 10/1983 |
| JP | 62-122634 | 6/1987 |
| JP | 7-507955 | 9/1995 |
| WO | WO 94/02065 | 2/1994 |
| WO | WO 2014/111779 A1 | 7/2014 |

OTHER PUBLICATIONS

International Search Report for International Application No. PCT/EP2015/079523, dated May 18, 2016.
Written Opinion of the International Searching Authority for International Application No. PCT/EP2015/079523.

* cited by examiner

APPARATUS AND METHOD FOR NON-INVASIVELY DETERMINING THE CONCENTRATION OF AN ANALYTE

This application is a national stage filing under 35 U.S.C. § 371 of International Application No. PCT/EP2015/079523, filed on Dec. 14, 2015, which claims priority of Danish Patent Application No. PA 2014 00725, filed Dec. 15, 2014. The contents of these applications are each incorporated herein by reference.

TECHNICAL FIELD

Embodiments of the apparatus and method disclosed herein relate to the field of noninvasively measuring an analyte concentration in a subject and, in particular, to the measurement of the partial pressure of carbon dioxide ($CO_2$) or other blood gases at a location of a subject's tissue such as a subject's skin, e.g. on an ear lobe.

BACKGROUND

The non-invasive measurement of the partial pressure of blood gases such as carbon dioxide ($pCO_2$) or oxygen ($pO_2$) by means of a sensor applied to the skin has been described in many publications as a useful tool in a number of clinical situations.

In prior art sensors, as e.g. described in U.S. Pat. No. 7,474,908 or 5,425,868, the gas is measured with a sensor applied to the surface of the skin, which is equipped with a heating element for heating the area of skin on which the sensor rests. The sensor contact surface is heated to a temperature of about 40° C. to 44° C. which results in a local vasodilation and arterialization of the capillary bed at the measurement site. Under these conditions, the $CO_2$ partial pressure measured by a sensor placed on a subject's skin shows a high correlation with the arterial values of $CO_2$. This makes it possible to determine and/or monitor the arterial $CO_2$ values with sufficient accuracy for most applications. The heating of the measurement site to such high temperatures involves the risk of skin burns or other undesired side effects, especially when a continuous monitoring of $pCO_2$ is desired over a longer period of time.

Furthermore, for some purposes the vasodilation of the skin is unwanted as the purpose of the measurement is to determine the perfusion of the skin, or a change in the skin perfusion. For such purposes, it is advantageous to avoid changing the structure of the skin, such as heating the skin and the underlying tissue, to create local vasodilation.

WO 2011/024081 suggests the measurement of $pCO_2$ by means of a $pCO_2$ sensor applied to the patient's earlobe and heated to only 37° C. or less in order to asses tissue perfusion in a patient, especially for treatment follow-up and prognosis of septic shock. Even though this prior art method reduces the need for heating the measurement site to very high temperatures, it still involves heating the measurement site.

The prior art generally has the disadvantage that there is an energy flow between the sensor and the skin tissue of the patient, because of the thermal gradient between the sensor and the skin tissue. This temperature gradient creates a local vasodilation of the capillary bed at the measurement site.

It is generally desirable and, in particular in certain clinical situations and for certain measurements, to further avoid heating of the measuring site while maintaining a high accuracy of the resulting measurements. In particular, it is desirable to provide a measurement of blood gases that further reduces the influence of the measurement on the local perfusion or microcirculation.

In particular, in certain clinical conditions, e.g. during shock, the tissue's capability of heat removal may be diminished; in such situations, it may be particularly desirable to avoid unnecessary heating.

Moreover, when the measurements are intended to provide indications of the perfusion or microcirculation at the measurement site or when shock is to be detected, it would be desirable to monitor perfusion/microcirculation rather than to influence it by the heating.

SUMMARY

According to a first aspect, disclosed herein are embodiments of an apparatus for noninvasive measurement of an analyte concentration. Embodiments of the apparatus comprise: a first thermally conductive part and a first thermal sensor disposed at the first thermally conductive part, the first thermally conductive part being adapted for thermally connecting with the tissue of a patient, and the first thermal sensor being operable to determine a temperature indicative of a temperature at a location on a surface of a tissue of a patient. A second thermally conductive part, thermally insulated from the first thermally conductive part and a second thermal sensor disposed at the second thermally conductive part, and further comprising an analyte sensor operable to generate a sensor signal indicative of a concentration of the analyte and a heater operable to control a temperature of the second thermally conductive part.

Consequently, the apparatus stabilises the temperature of the analyte sensor such that there is substantially no heat flow between the tissue at the measurement location and the analyte sensor, i.e. at least a surface part of the analyte sensor and the location on the tissue are maintained in thermal equilibrium with each other.

As at least the surface part of the analyte sensor is kept in thermal equilibrium with the tissue, the measured temperature can be used to correct for all temperature dependencies of the analyte sensor. In particular, current electrochemical $pCO_2$ sensors include temperature-dependent components such as a pH electrode, a reference electrode, an electrolyte and/or different membranes covering the electrolyte. Also, the part of the apparatus that is positioned on the subject's tissue may comprise other temperature-dependent components, such as an electronic circuit for signal amplification of the measured signals. These may also be corrected based on the determined temperature. The conversion of the sensor signal to a calculated analyte concentration associated with a predetermined reference temperature is based on the determined temperature. As the sensor is maintained in thermal equilibrium, the determined temperature corresponds to the tissue temperature and to the sensor core temperature; consequently, the conversion may compensate for all relevant temperature effects.

In the context of $pCO_2$ measurements, these may include temperature effects on the pH electrode potential, slope, and a temperature correction factor for the $pCO_2$. In some embodiments, the analyte sensor is operable to generate a sensor signal, and the processor is adapted to compute a calculated analyte concentration based on at least the sensor signal and on a sensor calibration function. In some embodiments, the apparatus comprises a storage medium for storing temperature calibration data indicative of a temperature-dependent calibration function, and the processor is adapted to compute the analyte concentration based on the sensor signal and on the stored temperature calibration data. The stored temperature calibration data may be stored in a variety of ways, such as in the form of one or more interpolation tables, one or more calibration functions, and/or in another suitable form. The calibration of the sensor signal may be performed by any suitable calibration process as is known as such in the art. In some embodiments, the calibration is performed at least in part at higher temperature (higher than 37° C.) so as to reduce the duration of the calibration process.

Hence, embodiments of the apparatus described herein automatically adjust the temperature of the analyte sensor to the tissue temperature. When the sensor is located on the skin of the subject, the thermal equilibrium is generally obtained at a temperature less than 37° C. The risk for skin burns and other undesired effects of heating of the subject's tissue are avoided while maintaining a high accuracy of the determined analyte concentration.

Generally, the measurement location on the subject's tissue may be a location on the subject's skin, e.g. on the subject's earlobe or another suitable measurement location. Alternatively, the sensor may be positioned on an inner surface of a body cavity or another tissue surface. The analyte sensor may generally be configured to measure the analyte concentration in the tissue and/or at a surface of the tissue.

The apparatus may output the resulting calculated analyte concentration as an analogue and/or digital output signal and/or in any other suitable form. In some embodiments, the apparatus comprises a display operable to display the calculated analyte concentration value, the determined temperature, or both. In some embodiments, the apparatus is configured to monitor the analyte concentration over time.

In some embodiments, the analyte is $CO_2$ and the analyte concentration is the partial pressure of $CO_2$ ($pCO_2$). Consequently, in such an embodiment the analyte sensor comprises a $pCO_2$ sensor, e.g. an electrochemical sensor, an optical sensor or another suitable form of sensor. In some embodiments, the sensor comprises a pH electrode. It will be appreciated, however, that other embodiments of the apparatus described herein may be used for measuring other types of analyte concentrations, such as a partial pressure of oxygen ($pO_2$) or of one or more other blood gases. In yet other embodiments, the apparatus may be operable to measure multiple analytes, e.g. both $CO_2$ and $O_2$.

Embodiments of the apparatus described herein may be used for the determination of cutaneous $pO_2$ measurements to determine the $O_2$ level of the capillary bed without local vasodilation and arterialization and thus—in combination with other sensor systems—to obtain additional information about the $O_2$ uptake of the tissue in a nonarterialized capillary bed. The same heating-control system described herein can also be applied for other non-invasive sensor systems, especially for sensors designed to measure the grade of micro-vascularization, e.g. Laser-Doppler, or sensors based on NIRS technology as $StO_2$.

The predetermined reference temperature may be any suitable temperature, e.g. a temperature between 22° C. and 38° C., such as between 32° C. and 38° C., such as between 32° C. and 35° C., or between 35° C. and 38° C., such as 37° C. The reference temperature depends on the level of activity of the person, the surroundings, e.g. whether the skin is covered or bare, and the surrounding temperature and cooling effect of e.g. wind. The temperature also depends on where on the human body, the sensor is located, e.g. a foot may only have a temperature a few degrees above the room temperature, whereas more centrally located body parts will have a temperature closer to the internal body temperature.

The first thermal sensor may be arranged such that it is in thermally conductive connection with the measurement location on the surface of the tissue so as to allow the first thermal sensor to determine the temperature at said measurement location on the tissue. The thermal conductive connection should have a thermal conductivity sufficiently high to allow a potential temperature gradient between the tissue surface and the immediate surrounding of the first thermal sensor to be equalised. Hence, the temperature measured by the first thermal sensor is indicative of the temperature at the measurement location on the tissue and the first thermal sensor can detect temperature changes of the tissue during the measurement. To this end, the first thermal sensor may be embedded in a thermally conductive part which may be in direct contact with the tissue during operation or which may be separated from the tissue by components, e.g. one or more membranes or other thin layers, that do not prevent the first thermal sensor from detecting temperature variations of the tissue. Generally, the first thermally conductive part may be in thermally conductive connection with the measurement location. Nevertheless, the first thermal sensor does not need to be in direct contact with the measurement location on tissue in order to measure a temperature indicative of the temperate at the location on the tissue.

In some embodiments, the apparatus comprises a second thermal sensor operable to measure a temperature indicative of a temperature of at least a part of the analyte sensor; and wherein a controller is configured to adjust the heater so as to adjust the temperature of said part of the analyte sensor to the temperature measured by the first thermal sensor. In some embodiments, the apparatus comprises:

first and second thermally conductive parts which are thermally insulated from each other; and a second thermal sensor disposed at the second thermally conductive part, wherein the heater is disposed at the second thermally conductive part and the first thermal sensor is disposed at the first thermally conductive part; and wherein the controller is operable to adjust the heater to maintain the heat differential between the first and second thermally conductive parts to essentially zero. In some embodiments, the second thermally conductive part is arranged to be thermally insulated from the subject's tissue during use of the apparatus while the first thermally conductive part is less insulated from the subject's tissue than the second thermally conductive part, so as to allow a faster heat exchange between the tissue and the first thermally conductive part than between the tissue and the second thermally conductive part. In some embodiments, the first thermally conductive part may be in direct contact with the subject's tissue, e.g. the subject's skin. In other embodiments, the first thermally conductive part may be separated from the tissue by one or more membranes or similar one or more thin layers. In one embodiment, the first and second thermally conductive parts may be embodied as first and second thermally conductive layers sandwiching a thermally insulating layer. The heater and/or the second thermal sensor may be disposed at the second thermally conductive part by embedding the heater and/or the second thermal sensor within the second thermally conductive part and/or by otherwise arranging the heater and/or the second thermal sensor in thermal contact with the second thermally conductive part. Similarly, the first thermal sensor may be disposed at the first thermally conductive part by embedding the first thermal sensor within the first thermally conductive part and/or by otherwise arranging the first thermal sensor in thermal contact with the first thermally conductive part. The apparatus may be configured to control the heater based on a difference of the temperature signals from the first and the second thermal sensors. The analyte sensor may be arranged such that at least a part of the analyte sensor is embedded in or in thermal contact with the second thermally conductive part such that a core temperature of the analyte sensor is controllable by the heater. It will be appreciated, however, that a part of the analyte sensor may also extend into or even through the first thermally conductive part.

Consequently, when the temperature of both thermal sensors is identical, this indicates that the sensor core temperature where the analyte sensor—e.g. the pH-electrode/electrolyte/reference electrode of a $pCO_2$ sensor—is located is at the same temperature as the tissue, thus indicating thermal equilibrium.

In some embodiments, a heater is only required in the second thermally conductive part, while no heater is required in the first thermally conductive part that is in thermal communication with the subject's tissue. Thus, the heater merely prevents a heat flow from the subject's tissue into the core of the sensor and further via the casing of the sensor head into the surroundings and/or via the cables connecting the sensor head that is in contact with the subject's skin to other parts of the apparatus, such as a control unit. Consequently, in some embodiments, the first thermally conductive part comprises no heater.

In some embodiments, the controller is operable to continuously adjust the heater to maintain the heat differential between the first and second thermally conductive parts to essentially zero. In particular, the apparatus may be configured to perform the temperature control concurrently with the measurement of the analyte concentration. The temperature control may be performed continuously. Maintaining the heat differential to essentially zero is intended to refer to a control mechanism operable to reduce the temperature differential to zero or at least below a small threshold, e.g. below 0.1° C.

In some embodiments, one or both of the first and second thermally conductive parts comprise silver and/or another suitable material such as gold. The thermally insulating material separating the first and second thermally conductive parts from each other may comprise an epoxy or another suitable material, such as a suitable polymer. The thermally insulating layer has a thickness sufficient for obtaining suitable heat insulation between the first and the second thermally conductive parts. In some embodiments the thickness of the heat insulating layer is at least 0.5 mm. Generally, the material of the thermally insulating layer may have a lower thermal conductivity than the material or materials of the thermally conductive parts. In some embodiments the first and/or second thermally conductive part(s) is/are made from a material with a thermal conductivity of more than 10 W/(m*K), such as 100 W/(m*K) or higher, and which does not interfere with the analyte sensor. The thermally insulating material may have a thermal conductivity of 1 W/(m*K) or less such as of 0.5 W/(m*K) or less.

In another embodiment, the apparatus comprises:
a first thermal sensor, the first thermal sensor being operable to measure a temperature of the tissue at a reference location;
an analyte sensor operable to measure the analyte concentration at a measurement location; wherein the second thermal sensor is operable to measure a temperature indicative of a temperature of at least a part of the analyte sensor;
wherein the controller is configured to adjust the heater so as to adjust the temperature of said part of the analyte sensor to the temperature measured by the first thermal sensor.

The first thermal sensor may be integrated into the same sensor head as the analyte sensor, attached to, extend from or otherwise arranged to be positioned with the analyte sensor as a single unit but operable to measure the temperature at a reference location different from the measurement location. The reference location and the measurement location may be adjacent locations on the surface of the tissue. Alternatively, the first thermal sensor may be provided as a separate sensor head which may be placed separately from the sensor head that comprises the analyte sensor. For example, in one embodiment, the apparatus comprises:
a first device comprising the first thermal sensor, the first thermal sensor being operable to measure a temperature of the tissue at said reference location, e.g. a cutaneous temperature;
a second device, separate from the first device, comprising the analyte sensor, the heater and a second thermal sensor operable to measure a temperature of the second device;
wherein the controller is configured to adjust the heater so as to adjust the temperature of the second device to the temperature measured by the first thermal sensor. Hence, according to this embodiment, the first and second thermal sensors may be positioned in separate devices that may be separately positioned on the subject's tissue, e.g. in close proximity to one another.

The first and second thermal sensors may each comprise a thermistor or an optical sensor e.g. an IR thermal sensor, or another suitable thermal sensor.

The present invention relates to different aspects including the apparatus described above and in the following, corresponding methods, systems, and products, each yielding one or more of the benefits and advantages described in connection with the above-mentioned apparatus and/or one of the other aspects, and each having one or more embodiments corresponding to the embodiments described in connection with the above-mentioned apparatus and/or one of the other aspects.

In particular, disclosed herein are embodiments of a method for monitoring an analyte concentration in a patient, the method comprising:
measuring the temperature of a tissue of the patient at a reference location with a first temperature sensor;
placing a device at a measurement location on the tissue of the patient, wherein the device comprises a heater and an analyte sensor;
adjusting the temperature of the device so that a thermal equilibrium is maintained at said measurement location on the tissue; and
measuring a concentration of the analyte with the analyte sensor at said measurement location.

The reference location and the measurement location may be the same location or different locations, e.g. two locations adjacent to or otherwise in close proximity to each other, such that the temperature at the reference location is indicative of the temperature at the measurement location. The thermal equilibrium is maintained locally between the device and the tissue at the measurement location.

Embodiments of an apparatus for monitoring an analyte concentration in a patient may comprise a control unit and a sensor head connectable to the processing unit via a wired or wireless connection. To this end the sensor head may comprise a wireless communications interface operable to wirelessly communicate with a control unit such as a monitoring device. The wireless communications interface may comprise a Bluetooth transmitter/receiver or another suitable circuit. The sensor head is configured to be brought into contact with the patient's tissue at the measurement location. The sensor head may comprise the thermal sensor(s), the heater and the analyte sensor. The sensor head may further comprise a signal processing circuit including e.g. a signal amplifier and configured to output a sensor signal. The control unit may comprise the processor, e.g. a suitably programmed microprocessor, configured to receive the sensor signal and to perform the conversion of the received sensor signal to the computed analyte concentration. To this end, the control unit may comprise a storage medium, such as a hard disc, an EPROM, EEPROM, a flash disk, and/or the like for storing calibration data to be used in the conversion. The control unit may further comprise a user interface such as a display for presenting a graphical user interface and/or the like. The control unit may further comprise the controller for controlling the heater. The controller may be integrated in the microprocessor or other circuitry as the processor or it may be implemented as a separate hardware module. Alternatively, in some embodiments, some or all of the functionality of the processor and/or the controller may be implemented by circuitry included in the sensor head.

In a further aspect of the invention disclosed herein is a method for controlling the temperature of a device for non-invasive measurement of an analyte concentration in a patient, the method comprising: Measuring the temperature of a tissue of the patient with a first temperature sensor located in a first thermally conducting part of the device, the first thermally conducting part being in thermal connection with the tissue of the patient, and adjusting the temperature of a second thermally conducting part of the device, the second thermally conducting part being thermally insulated from both the tissue of the patient and the first thermally conducting part, to maintain a thermal equilibrium between the tissue, and the second thermally conducting part.

It has been a prejudice within the art that it is necessary to warm up the skin tissue, to dissolve the lipid structure of the dead keratinized cells in the epidermal layer to make the stratum corneum more permeable to blood gases, especially to make it more permeable to $O_2$ since $O_2$ does not easily diffuse through the epidermal layer. However there are ways to dissolve, or remove the epidermal layer, to allow the sensor to get in contact with the oxygen carrying cells. E.g. US 2013013795 A1 discloses a device that mechanically removes the epidermal layer until a predetermined value of impedance between two electrodes is reached. Once sufficient epidermal layers have been removed, a drug delivery composition or an analyte sensor is applied to the treated site.

It is noted that the conversion of the sensor signal into a computed analyte concentration may at least partly be implemented in software and carried out on a data processing system or other processing means caused by the execution of program code means such as computer-executable instructions. Here and in the following, the term processing means comprises any circuit and/or device suitably adapted to perform the above functions. In particular, the above term comprises general- or special-purpose programmable microprocessors, Digital Signal Processors (DSP), Application Specific Integrated Circuits (ASIC), Programmable Logic Arrays (PLA), Field Programmable Gate Arrays (FPGA), special purpose electronic circuits, etc., or a combination thereof. Alternatively, the described features may be implemented by hardwired circuitry instead of software or in combination with software.

The sensor head may be configured to be brought into contact with a tissue surface with a measuring surface of the first thermally conductive part facing the tissue surface and with the second thermally conductive part being separated from the tissue surface by at least the first thermally conductive part and a thermally insulating part insulating the first thermally conductive part from the second thermally conductive part. The sensor head may be operable to be placed on the tissue surface such that the first thermally conductive part is brought into thermal communication with the tissue, e.g. by bringing the measuring surface directly into contact with the tissue surface or via one or more membranes or surface layers covering the measuring surface of the first thermally conductive part. In some embodiments, at least a part of the analyte sensor is disposed at the second thermally conductive part.

BRIEF DESCRIPTION OF THE DRAWINGS

The above and other aspects will be apparent and elucidated from the embodiments described with reference to the drawing in which.

DETAILED DESCRIPTION

Figure 1:
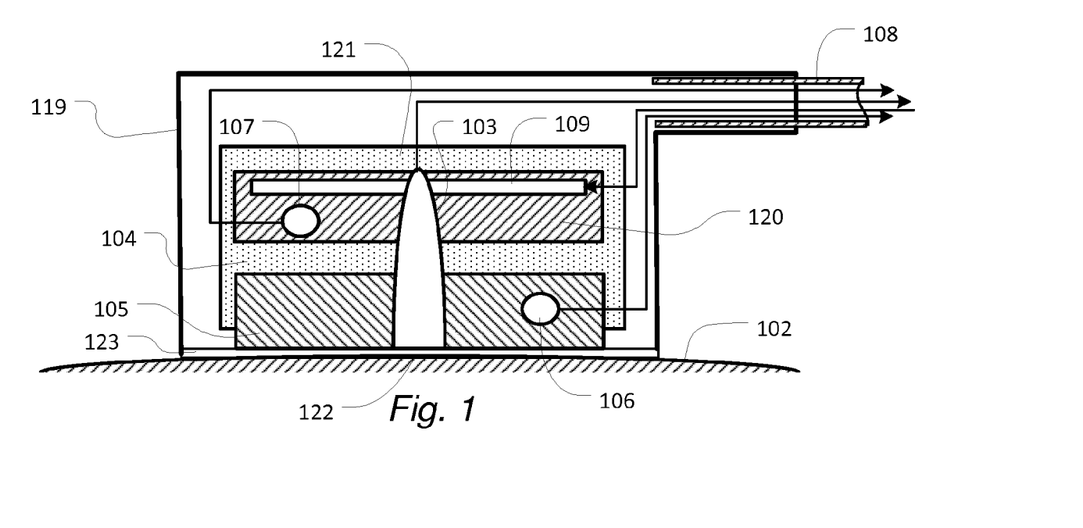
FIG. 1 shows a schematic block diagram of an example of a sensor head of an apparatus for non-invasively measuring $pCO_2$.

FIG. 1 shows a schematic block diagram of an example of a sensor head of an apparatus for non-invasively measuring $pCO_2$. The sensor head 101 comprises a sensor housing 119 of an electric insulating material, for example polyphenyleneoxide (PPO), into which first and second thermally conducting plates 105 and 120, respectively, are disposed. The plates 105 and 120 may be made of silver or gold or a material with similar or at least suitable thermal conductive properties, and which does not interfere with the chemical analysis. The thermally conducting plates may be embedded into and secured by an epoxy casting 121 which fills the void between the plates and the housing and which forms a thermally insulating layer 104 separating and sandwiched between the thermally conductive plates 105 and 120. The first thermally conducting plate 105 defines a measuring surface of the sensor head which, during operation, is arranged to face a subject's skin 102 at a desired measurement location. The second thermally conducting plate 120 is disposed in the central portion of the sensor head and, during operation, is separated from the subject's skin at least by the thermally insulating layer and by the first thermally conductive plate. Said insulating layer 104 thermally insulates the second thermally conducting plate 120 from the first thermally conducting plate and from the subject's skin so that the heat transfer gradient between, on the one hand, the second thermally conducting plate and, on the other hand, the first thermally conducting plate and the subject's skin is small. The insulating layer may e.g. be made from epoxy, or from polyurethane or from a polymer with similar thermal properties as epoxy. The measuring surface of the first thermally conductive plate 105 is covered by one or more thin layers 123. For example, the layers may comprise one or more of the following layers: an electrolyte layer—e.g. a spacer membrane soaked with electrolyte solution —, a Teflon membrane, a gold blade. An outer one of the layers 123, e.g. a gold blade, defines a contact surface which, during the measurement is brought into contact with the subject's skin 102. When placed with the contact surface in contact with the skin of the subject, a heat exchange occurs between the first thermally conductive plate and the subject's skin via the layers 123 until any temperature gradient between the skin and the first thermally conductive plate is substantially equilibrated.

The sensor head 101 is connectable to a control unit or monitor via a cable 108 that extends from a tubular extension of the housing 119 so as to allow remote control of the various functions relating to in vivo monitoring by the control unit/monitor, e.g. connecting/disconnecting current circuits, processing data, etc.

A first temperature sensor 106, e.g. in the form of an NTC resistor or other suitable thermistor, is embedded into—or at least in good thermal contact with—the first thermally conductive plate 105 and operable to measure a skin temperature of the skin 102 at the measurement site which is in contact with the contact surface. The temperature sensor 106 is glued to or into the first thermally conductive plate 105 by means of heat conductive glue and the thermal sensor is connectable to the controlling monitor via the cable 108.

A heating element 109, e.g. in the form of a Zener diode, is embedded into—or at least in thermal contact with—the second thermally conductive plate 120. The heating element 109 is operable to heat the second thermally conductive plate. A second temperature sensor 107, e.g. in the form or an NTC resistor or other suitable thermistor, is also embedded in—or at least in good thermal contact with—the second thermally conductive plate 120. The heating element 109 and the temperature sensor 107 are both glued to or into the second thermally conductive plate 120 by means of heat conductive glue and they are each connectable to the controlling monitor via the cable 108.

The sensor head further comprises a $pCO_2$ sensor 103 having a first portion that is arranged in the second thermally conductive plate 120 and another portion extending through the insulating layer 104 and the first thermally conductive plate 105 towards the contact surface and defining the measurement location 122. The $pCO_2$ sensor may be surrounded by a thermally insulating layer. The $pCO_2$ sensor 103 performs a $pCO_2$ measurement in a well-known manner based on measuring pH. To this end the $pCO_2$ sensor may comprise a pH glass electrode and a reference electrode such as an Ag/AgCl reference electrode. Both electrodes may comprise a part that is arranged in the second thermally conductive plate 120 and another part that extends through the insulating layer 104 and the first thermally conductive plate 105 towards the contact surface.

For example, the $pCO_2$ sensor may be embodied as described in U.S. Pat. No. 5,425,868 or 6,654,622, the entire contents of which are included herein by reference.

During operation of the sensor head, the heater element 109 is controlled to heat the second thermally conductive plate 120 such that the temperature of the second thermally conductive plate 120 as measured by thermal sensor 107 is the same as the temperature of the first thermally conductive plate 105 as measured by thermal sensor 106, so as to compensate for the cooling effect which the sensor otherwise would have on the tissue. When the temperature readings of both thermal sensors 106 and 107 are identical, this indicates that the temperature of the sensor core including, in particular, the $pCO_2$ sensor 103, e.g. the pH-electrode/electrolyte/reference electrode at the same temperature as the tissue below the skin 102 (temperature equilibrium).

It will be appreciated that the sensor head may comprise additional sensors, e.g. a $pO_2$ sensor, and/or other components, e.g. an electronic circuit for pre-processing the sensor signal from the $pCO_2$ sensor 103 and/or from the thermal sensors. Such preprocessing may include a pre-amplifier and/or circuitry for generating a difference signal between the temperature signals from the thermal sensors.

Figure 2:
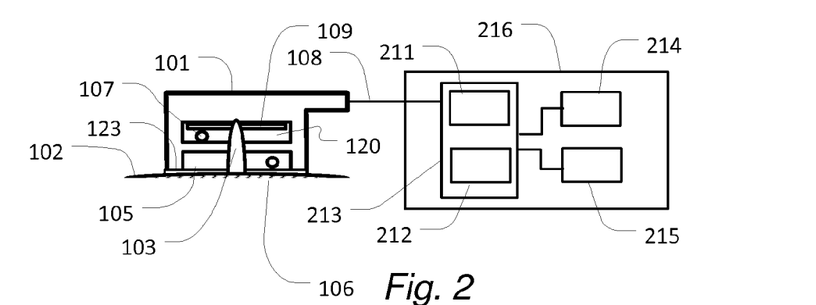
FIG. 2 shows a schematic block diagram of an example of an apparatus for non-invasively measuring $pCO_2$.

FIG. 2 shows a schematic block diagram of an example of an apparatus for measuring transcutaneous $pCO_2$. The apparatus comprises a sensor head 101 and a control unit 216 to which the sensor head 101 is connected via cable 108. Alternatively, the sensor head may be connected to the control unit via a wireless interface, e.g. using Bluetooth or another short-range radio-frequency communication technology. The sensor head may be the sensor head shown in FIG. 1. The control unit 216 comprises a processing unit 213 as well as a user interface 214 and a data storage device 215, both communicatively coupled to the processing unit. The processing unit 213 may be any suitably programmed CPU or microprocessor or other suitable processing means. The data storage device 215 may be a RAM, an EPROM, a hard disk, or another suitable device for storing program and/or other data. The user interface 214 may include a display such as a touch screen for displaying information, selectable menu items allowing a user to select operational options, enter parameters, and/or the like. The user interface may be operable to present measurement results to the user, to request user inputs or other user actions, to present selectable options and/or to present instructions to the user. The user interface may further comprise a keypad, buttons, and/or user interface devices.

The processing unit 213 comprises a signal processing block 211 and a control block 212. Though shown as separate blocks in FIG. 2, the signal processing block 211 and a control block 212 may be implemented in a variety of ways, e.g. as separate hardware modules, as separate functional blocks implemented by a common processor or even as a single functional block. During operation, the processing unit 213 receives a sensor signal from the $pCO_2$ sensor in the sensor head 101 and temperature signals from the thermal sensors in the sensor head 101.

Based on the temperature signals, the control block 212 controls the heater of the sensor head so as to maintain the difference between the temperatures measured by the first and second temperature sensors as close to zero as possible. For example, the heater may be controlled by a difference signal indicative of the difference between the temperature signals from the first and the second thermal sensors.

Since the sensor is normally exposed to ambient air before applying it on a patient, the temperature measured by both thermal sensors is the temperature of the ambient air.

Then, when the sensor is brought into contact with the skin with its contact surface, the thermal sensor 106 located in the first thermally conductive part 105 close to the sensor's contact surface will be heated by the tissue to a temperature T1. At this time, the temperature T2 measured by the other thermal sensor 107 is typically lower (T2<T1) and the control block 212 will cause the heater 109 to heat the core portion of the sensor head (i.e. T2 will increase) until the temperatures become equal T2=T1 (or at least equal within a predetermined margin ΔT, i.e. |T2−T1|<ΔT). The control unit 212 continuously adjusts the heater in order that both temperatures are identical. If the tissue temperature decreases, the temperature T1 will be lower than T2 and the heating power will be reduced or even turned off until both temperatures are identical again. If the tissue temperature increases, more heating power will be delivered to the heater in order that T1=T2.

Based on the sensor signal from the $pCO_2$ sensor and the temperature signal from at least one of the thermal sensors (at equilibrium, the sensor core temperature Tcore is equal to T1 and T2), the signal processing block 211 computes a calculated partial $CO_2$ pressure. To this end, the signal processing block may apply a predetermined calibration formula that may depend on one or more temperature-dependent parameters. The calibration formula including the temperature-dependent parameters may be stored in the storage device 215 of the control unit 216. The processing unit may display the calculated $pCO_2$ on its display 214 and, optionally, the determined temperature and/or an indication as to whether the sensor head is in thermal equilibrium with the skin (|T2−T1|<ΔT).

Figure 4:
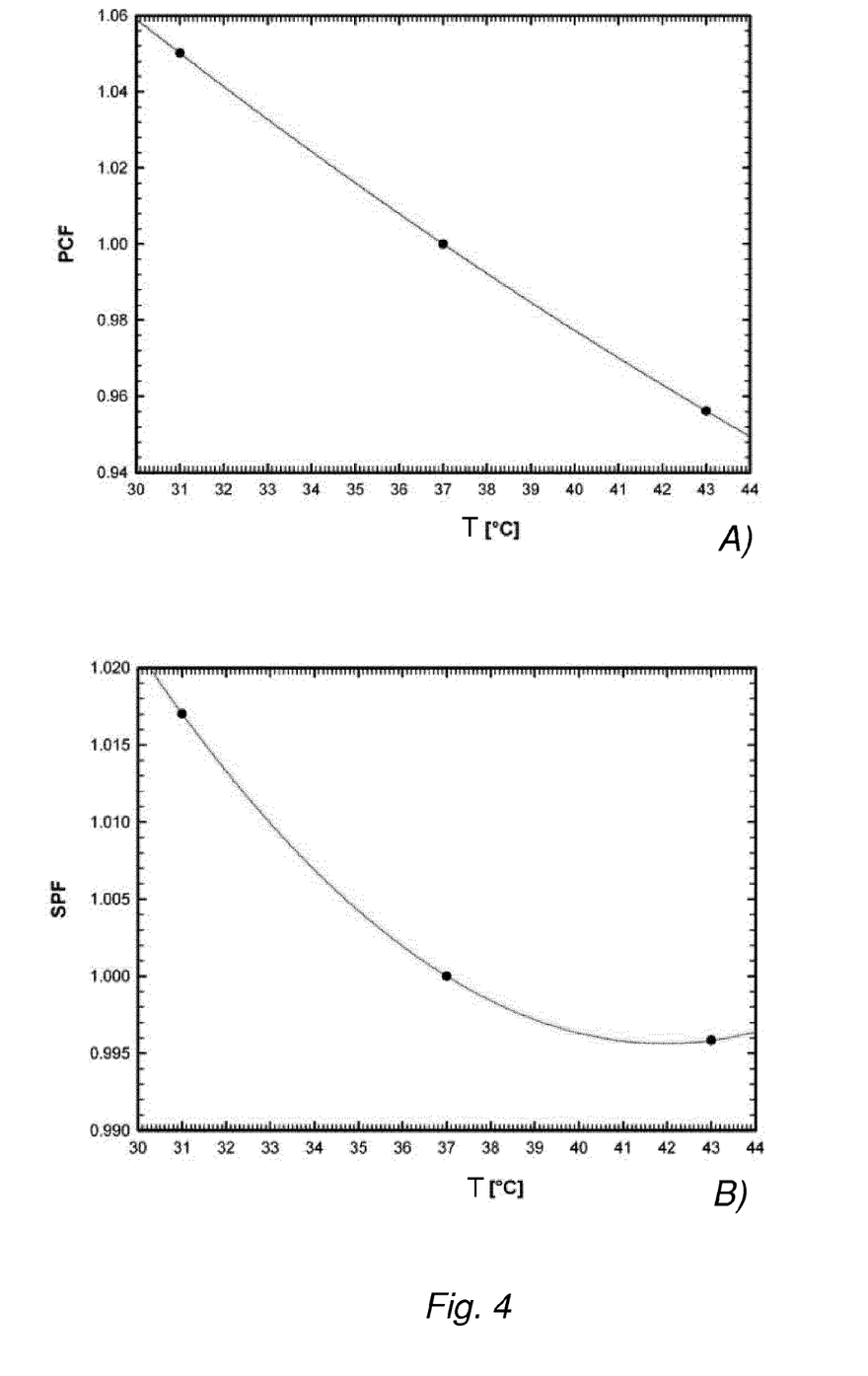
FIGS. 4A-B show examples of regression functions for temperature-dependent calibration terms PCF(T) and SPF(T), respectively, as obtained from experimental data and used in an example of the conversion of the sensor signal into a calculated $pCO_2$ value.

The computation of the $pCO_2$ value may e.g. be based on the equation $$pCO2 = C * \exp\left(\frac{MP*PCF - CP}{SCF*(CP - SP)}\right)$$

Where C is an overall constant, MP is the measured potential by the $pCO_2$ sensor, PCF is a temperature-dependent correction factor, CP is the calibration potential, SCF is a temperature-dependent slope correction factor and SP is the slope potential. The temperature-dependence of the correction factors for the potential (PCF (T)) and the slope (SFC(T)) may be determined from experimental data by means of a suitable regression. FIGS. 4A-B show examples of regression functions for PCF(T) and SPF(T), respectively, as obtained from experimental data.

Figure 3:
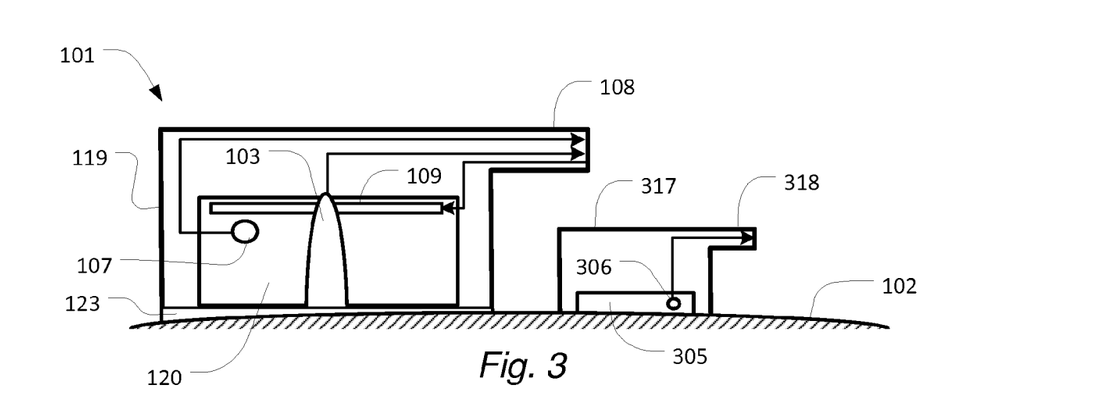
FIG. 3 shows a schematic block diagram of an example of a two-piece sensor head of an apparatus for non-invasively measuring $pCO_2$.

FIG. 3 shows a schematic block diagram of an example of a two-piece sensor head of an apparatus for non-invasively measuring $pCO_2$. In this example, the first thermal sensor is implemented as a second, separate sensor head 317 which may be positioned on the subject's skin separately from the sensor head 101 that comprises the $pCO_2$ sensor. Alternatively, the second sensor head with the first thermal sensor may be attached to a side of the sensor head 101 or otherwise extend from the sensor head 101. In any event, in such embodiments, the thermal sensor measures a temperature of the skin at a reference location adjacent to but in close proximity from the measurement site under the sensor head 101. As in the previous example, the sensor head 101 comprises a thermally conductive layer 120 comprising a heater element 109, a thermal sensor and a part of the $pCO_2$ sensor 103. The second sensor head 317 comprises a separate thermal sensor 306 embedded in a thermally conductive layer 305. Alternatively, the second sensor head may include a thermal sensor that uses another temperature measurement technique, e.g. based on infrared light. As in the previous example, the heater may be controlled to maintain the $pCO_2$ sensor at a temperature equal to the temperature measured with the thermal sensor 305 of the second sensor head 317.

Figure 5:
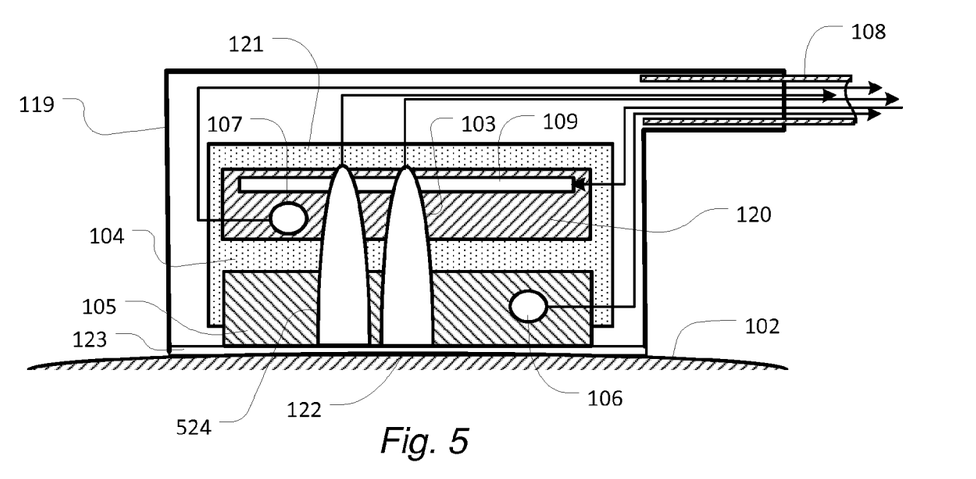
FIG. 5 shows a schematic block diagram of an example of a sensor head of an apparatus for non-invasively measuring $pCO_2$ and $pO_2$.

FIG. 5 shows a schematic block diagram of an example of a sensor head of an apparatus for non-invasively measuring $pCO_2$ and $pO_2$. The sensor head 101 is similar to the sensor head shown in FIG. 1 and it comprises many of the same components as the sensor head 101 of FIG. 1. These are designated by the same reference numerals and will not be described again. The sensor head 101 of FIG. 5 further comprises a $pO_2$ sensor 524, e.g. in the form of a platinum cathode which may be embedded in glass. The $pO_2$ sensor 524 has a first portion that is arranged in the second thermally conductive plate 120 and another portion extending through the insulating layer 104 and the first thermally conductive plate 105 towards the contact surface and defining the measurement location 122. The $pO_2$ sensor 524 performs a $pO_2$ measurement in a well-known manner. In one embodiment, the $pO_2$ sensor is an amperometric sensor and the sensor comprises a reference electrode (not explicitly shown) operable to create an electrical circuit between the $pO_2$ sensor and the reference electrode. In embodiment of FIG. 5, the thermally conducting layers are preferably made from gold or from another material that does not easily oxidize.

Figure 6:
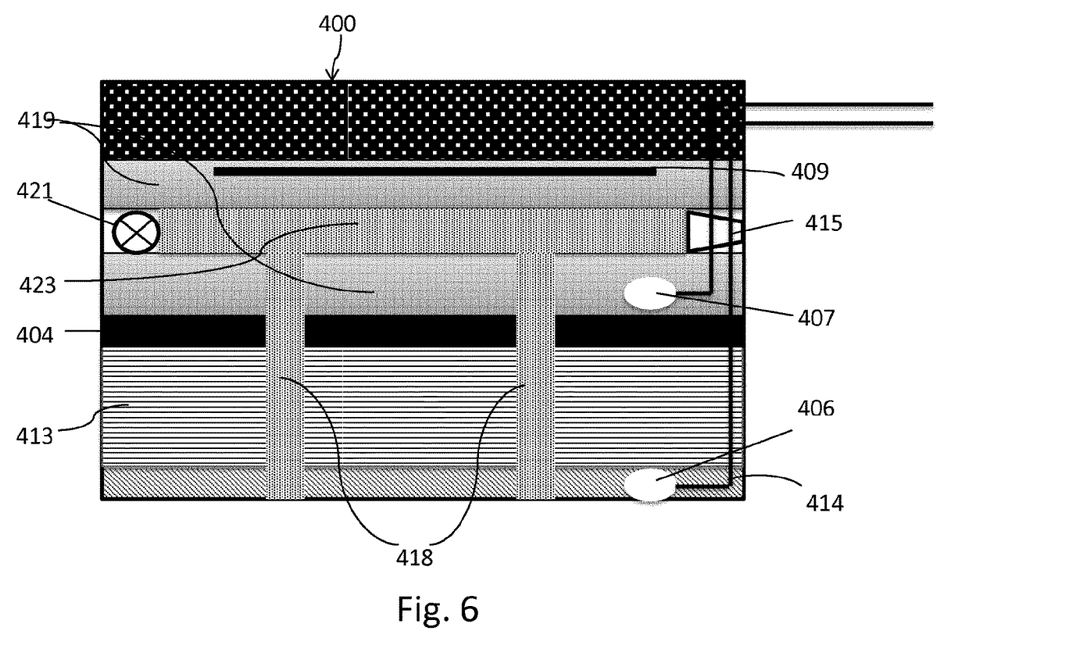
FIG. 6 shows a schematic block diagram of an example of a sensor head of an apparatus for non-invasively measuring $pCO_2$, using an optical principle.

FIG. 6 shows a further embodiment of the invention, wherein the sensor head (400) uses an optical principle for measuring the gas concentration. The sensor head (400) contacts the tissue of a patient through the thin metal layer (414) covering the membrane (413) acting as a patient interface. The thin metal layer (414) acts as a first thermally conducting part and is insulated from the second thermally conducting part (419) by at least the isolating layer (404). Two chimneys (418) allows the gases flowing out through the tissue of a patient to enter the measuring chamber (423), closed at one end by a light source (421) and at the opposite end by the dual channel detector (415), whereby the tissue of the patient, the chimneys (418) and the measuring chamber (423) define a closed system. A further thermal sensor (407) is located in a thermally conducting part (419), which may be used to regulate the temperature of the sensor by regulating the power supplied to a heating element (419). In this way, the temperature of the thermally conducting part (417) may be regulated to have essentially the same temperature as measured with the thermal sensor (406), consequently there is no substantial heat flow between the tissue of a patient and the sensor (400).

Although some embodiments have been described and shown in detail, the invention is not restricted to them, but may also be embodied in other ways within the scope of the subject matter defined in the following claims.

The method, product means, system, and device described herein can be implemented by means of hardware comprising several distinct elements, and/or partly or completely by means of a suitably programmed microprocessor. In the device claims enumerating several means, several of these means can be embodied by one and the same item of hardware, e.g. a suitably programmed microprocessor, one or more digital signal processor, or the like. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A sensor head for an apparatus for non-invasive measurement of an analyte concentration in a patient, the sensor head comprising:
a first thermally conductive part and a first thermal sensor disposed at the first thermally conductive part;
the first thermally conductive part being adapted for thermally connecting with the tissue of the patient;
the first thermal sensor being operable to determine a temperature indicative of a temperature at a location on a surface of a tissue of the patient;
a second thermally conductive part, thermally insulated from the first thermally conductive part;
a second thermal sensor disposed at the second thermally conductive part;
an analyte sensor operable to generate a sensor signal indicative of a concentration of the analyte;
a heater operable to control a temperature of the second thermally conductive part, and
a controller that controls the power supplied to the heater to minimize a temperature difference between the temperatures determined by the first and second thermal sensors.

2. The sensor head according to claim 1, wherein the first thermally conductive part comprises a first thermally conductive layer defining a surface which during use faces the skin of the subject, said first thermally conductive layer comprising the first thermal sensor; wherein the second thermally conducting part comprises a second thermally conductive layer comprising the second thermal sensor and the heater; and wherein the sensor head comprises an insulating layer operable to thermally insulate the second thermally conductive layer from the first thermally conductive layer.

3. The sensor head according to claim 2; wherein the analyte sensor is disposed in thermal contact with the second thermally conductive layer.

4. The sensor head according to claim 1, wherein the first and second thermal sensors are operable to determine a temperature difference between respective temperatures of the first and second thermally conductive parts.

5. The sensor head according to claim 1 wherein the analyte is $CO_2$; the analyte concentration is the partial pressure of $CO_2$ ($pCO_2$), and the analyte sensor is a $pCO_2$ sensor.

6. The sensor head according to claim 5, wherein the $pCO_2$ sensor comprises a pH electrode.

7. The sensor head according to claim 5, wherein the $pCO_2$ sensor comprises an optical measuring chamber.

8. The sensor head according to claim 1, wherein the sensor head further comprises a processor configured to convert the sensor signal to a calculated analyte concentration value.

9. The sensor head according to claim 1, wherein the first and second thermally conductive parts are embodied as first and second thermally conductive layers sandwiching a thermally insulating layer.

10. A system for non-invasive measurement of an analyte concentration comprising:
a sensor head according to claim 1;
a monitor for monitoring the analyte concentration value, comprising
a processor configured to convert the sensor signal to a calculated analyte concentration value; and
a controller operable to receive a temperature signal from at least the first thermal sensor and to adjust the heater to maintain a thermal equilibrium between at least the analyte sensor and the measurement location on the tissue.

11. The system according to claim 10, wherein the controller is operable to adjust the heater to maintain a thermal equilibrium at the measurement location on the tissue at a temperature equal to or less than 37° C.

12. The system according to claim 10, further comprising a display operable to display the calculated analyte concentration value, a determined temperature, or both.

13. The system according to claim 10, wherein the analyte is $CO_2$; wherein the analyte concentration is the partial pressure of $CO_2$ ($pCO_2$), and wherein the analyte sensor is a $pCO_2$ sensor.

14. The system according to claim 10, wherein a predetermined reference temperature is between 35° C. and 38° C.

15. The system according to claim 10, wherein the controller is operable to continuously adjust the heater to maintain the heat differential between the first and second thermally conductive parts to essentially zero.

16. A method of detecting shock in a patient, the method comprising:
non-invasively measuring an analyte concentration in the patient using the sensor head according to claim 1.

17. A method of detecting shock in a patient, the method comprising:
non-invasively measuring an analyte concentration in the patient using the system according to claim 10.

18. A method for controlling a temperature of a device for non-invasive measurement of an analyte concentration in a patient, the method comprising;
measuring a temperature of a tissue of the patient with a first temperature sensor located in a first thermally conductive part of the device, the first thermally conductive part being in thermal connection with the tissue of the patient;
adjusting the temperature of a heating element disposed at a second thermally conductive part of the device, the second thermally conductive part being thermally insulated from the first thermally conductive part, to maintain a thermal equilibrium between the tissue and the second thermally conductive part.

* * * * *